(12) United States Patent
Reuben

(10) Patent No.: US 9,024,770 B2
(45) Date of Patent: May 5, 2015

(54) ELECTRONIC FOOTBALL CONCUSSION AVOIDANCE TRAINING MODULE

(71) Applicant: David Isidore Reuben, Las Vegas, NV (US)

(72) Inventor: David Isidore Reuben, Las Vegas, NV (US)

(*) Notice: Subject to any disclaimer, the term of this patent is extended or adjusted under 35 U.S.C. 154(b) by 207 days.

(21) Appl. No.: 13/764,897

(22) Filed: Feb. 12, 2013

(65) Prior Publication Data

US 2014/0223990 A1    Aug. 14, 2014

(51) Int. Cl.
- *A61B 5/00* (2006.01)
- *G01L 1/00* (2006.01)
- *A63B 1/00* (2006.01)

(52) U.S. Cl.
CPC ............ *G01L 1/00* (2013.01); *A61B 5/6803* (2013.01); *A63B 1/00* (2013.01)

(58) Field of Classification Search
USPC ................. 340/665; 73/12.04; 2/422
See application file for complete search history.

(56) References Cited

U.S. PATENT DOCUMENTS

| | | | |
|---|---|---|---|
| 8,191,421 B2* | 6/2012 | Petelenz et al. | 73/579 |
| 2012/0105224 A1* | 5/2012 | Ford | 340/539.12 |
| 2012/0223833 A1* | 9/2012 | Thomas et al. | 340/539.12 |
| 2012/0309300 A1* | 12/2012 | Howard et al. | 455/39 |
| 2013/0282308 A1* | 10/2013 | Mack et al. | 702/41 |
| 2014/0088454 A1* | 3/2014 | Mack | 600/553 |
| 2014/0143940 A1* | 5/2014 | Iuliano et al. | 2/422 |
| 2014/0149067 A1* | 5/2014 | Merril et al. | 702/141 |

* cited by examiner

*Primary Examiner* — Albert Wong

(57) ABSTRACT

A self-contained removable electronic module which mounts onto an ordinary football helmet's face mask bars and visually annunciates to the wearing player and game referees the occurrence of a blow to the player's helmet of an impact exceeding a preselected threshold level.

16 Claims, 4 Drawing Sheets

ELECTRONIC FOOTBALL CONCUSSION AVOIDANCE TRAINING MODULE

DETAILED DESCRIPTION

FIGS. 1, 2, 3, and 4

Figure 1:
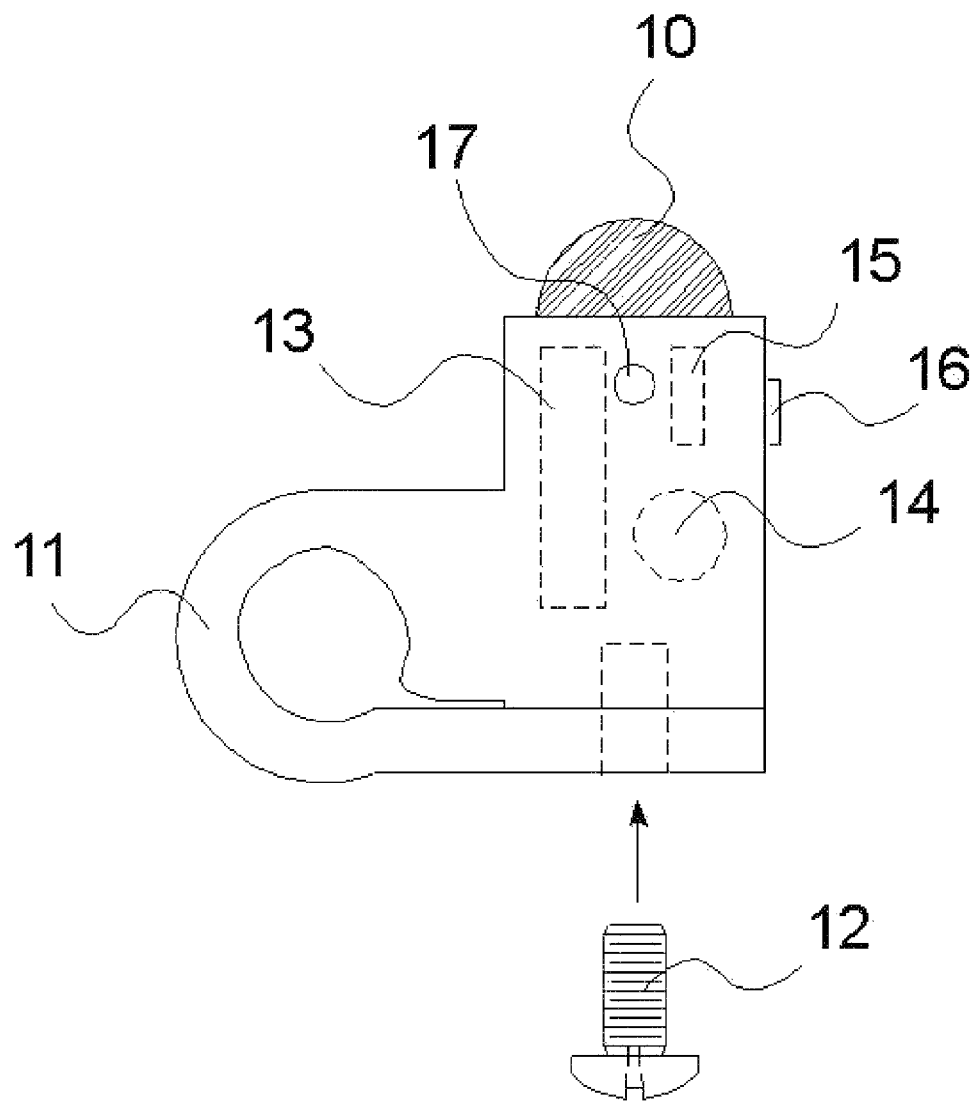

FIG. 1 shows a side view of the module. This embodiment discloses a loop strap 11 which wraps around a face mask bar and is tightened and secured by fastening screw 12. On top of the module is LED lamp 10. On the side of the module is shown manual reset button 17. On the front of the module is shown test pushbutton 16. Embedded in the module are battery 13 shock sensor 14 and timer 15.

Figure 2:
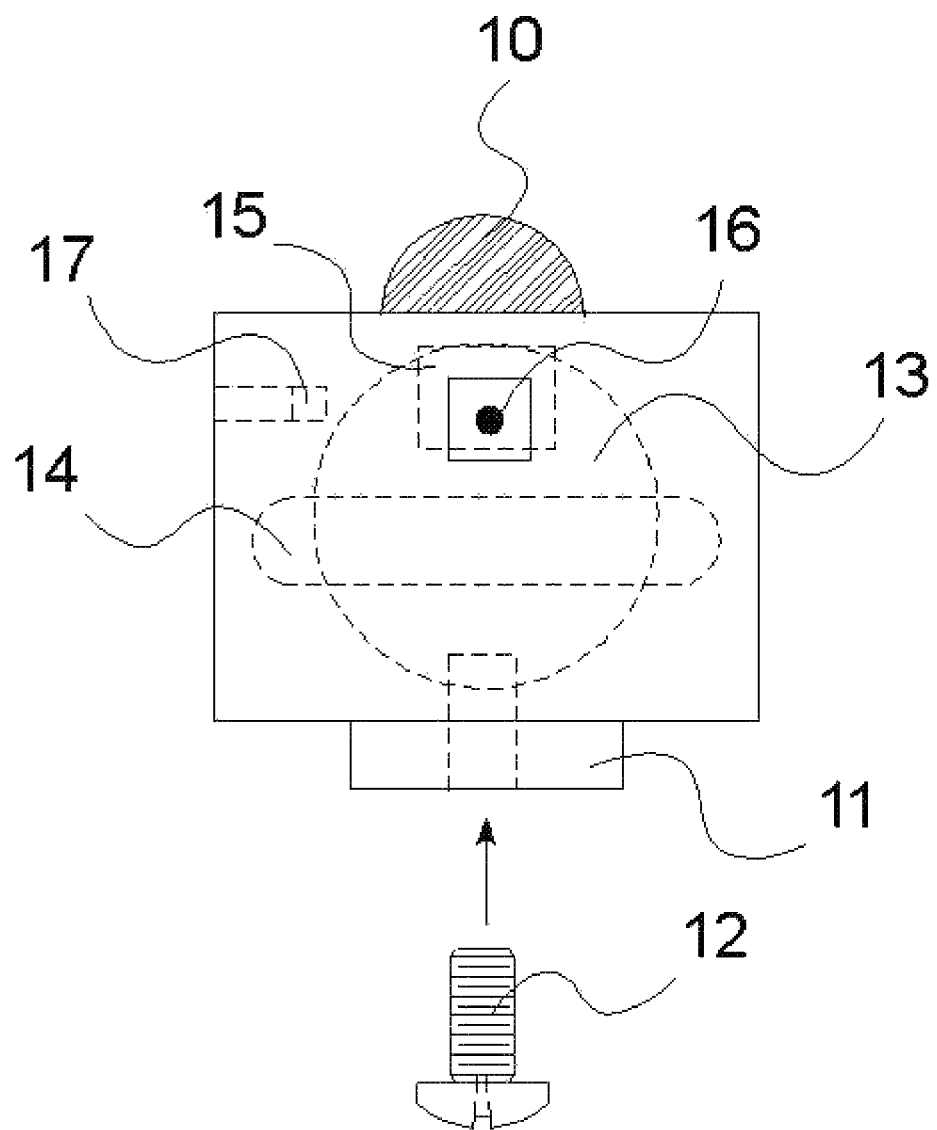

FIG. 2 shows the front of the module. This is the side facing the player. On the bottom is shown the loop strap 11 which is fastened to the module body by fastening screw 12. On top is shown the LED lamp 10. On the front of the module body is shown test pushbutton 16. Recessed into the side of the module body is shown manual reset button 17. Embedded in the module body are shown battery 13 shock sensor 14 and timer 15.

Figure 3:
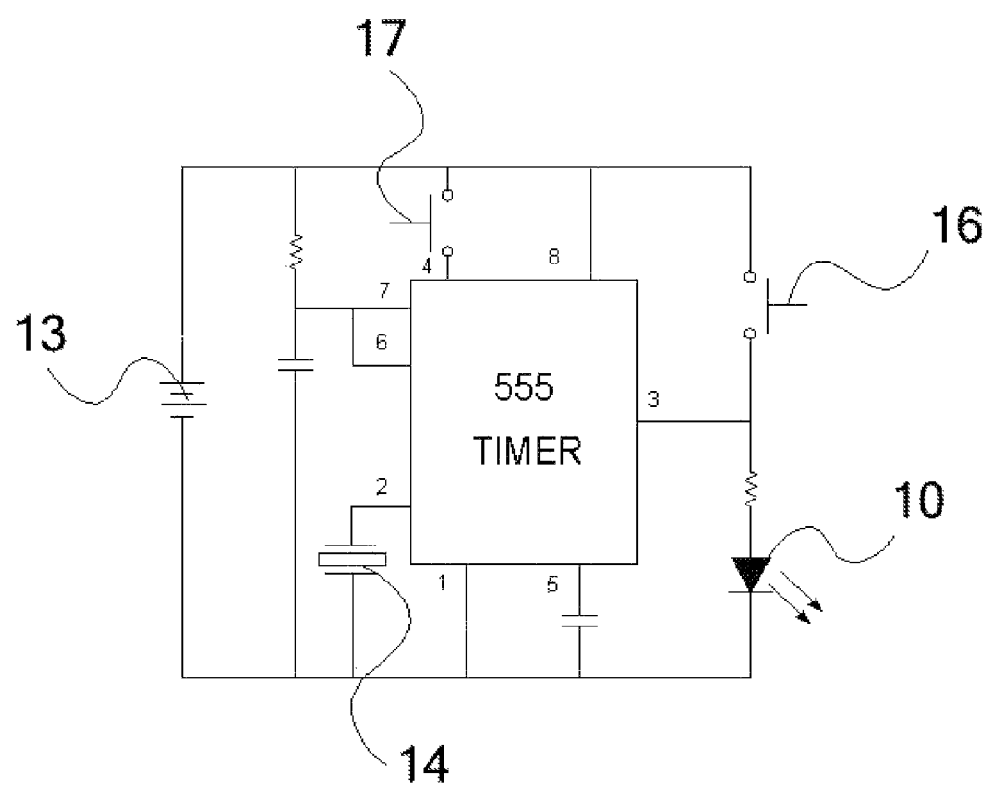

FIG. 3 shows a basic simplified circuit schematic. Included in the circuit are LED lamp 10, battery 13, shock sensor 14, timer 15, test pushbutton 16, and manual reset button 17. Additional circuitry may be required and would vary depending on the type of shock sensor specified such as piezoelectric.

Figure 4:
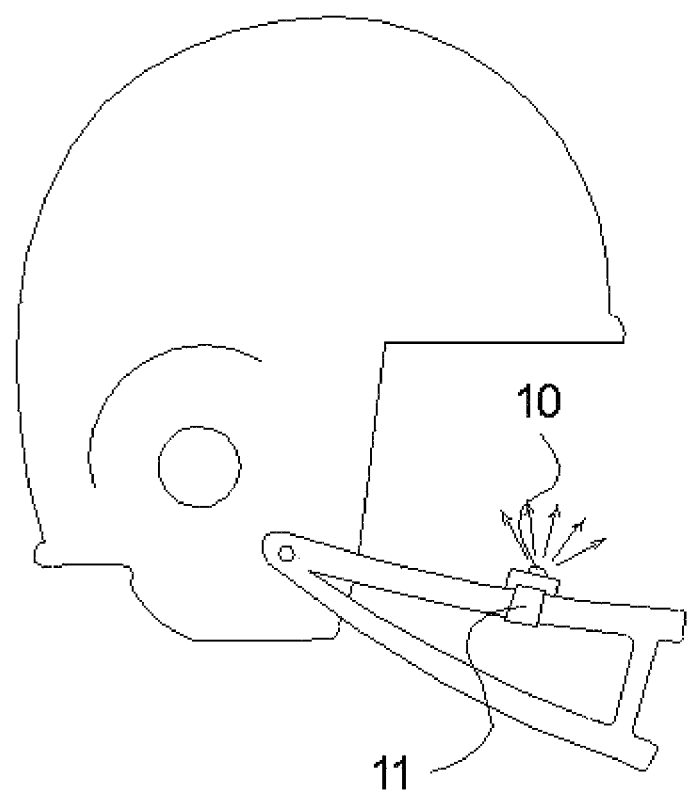

FIG. 4 shows the module mounted on a football helmet's face mask. Loop strap 11 is shown wrapped around the face mask bar. The LED lamp 10 is again shown at the top of the module. The LED lamp 10 is a type with 360 degree field of view. The light emitted from the LED lamp 10 is shown visible to both the player and game referees.

DETAILED DESCRIPTION

Operation

State of the art electronic components can be used in the module rendering the device sufficiently small so as to not interfere significantly with the players field of vision. The body can be made of a hard matt black rubber so as not to cause any glare.

The module can be tightly attached to the facemask bars on the inside of the football helmet's face mask where it would not be exposed to a direct hit but would sense any hit to the helmet.

The integrity of the battery charge is checked by pressing the test pushbutton which illuminates the LED.

The sensitivity of the sensor is to be such that it would not nuisance trigger but would trigger given a legitimate hit to the player's head.

Given a sufficient hit to the player's head the LED would illuminate for a preset time period of, for example, 45 seconds and then turn off automatically. In a second embodiment The LED must be turned off manually with a reset tool.

For practice, a higher sensitivity module can be used in order to train players to hit and tackle in a manner which avoids any direct impact to the head. An annunciation in practice would enable coaching staff to correct a player's technique.

For games, a lower sensitivity module can be used so that only hard hits to the head trigger an annunciation. An annunciation during a game enables the player hit to suspend play, enables the player hit to exit the game and be evaluated for concussion, and enables the referees to penalize or eject the hitting player.

The applicant proposes that rule book changes be made for games in which the module is used. For example, the player who suffers an annunciated hit be forced to sit out a play and be evaluated for concussion, and the hitting player be penalized for a first occurrence and be ejected for a second.

DRAWINGS

Figures

FIG. 1 Module Side
FIG. 2 Module Front
FIG. 3 Basic Circuit Schematic
FIG. 4 Helmet With Mounted Module

REFERENCE NUMERALS

10 LED tamp
11 Loop Strap
12 Fastening Screw
13 Battery
14 Shock Sensor
15 Timer
16 Test Pushbutton
17 Manual Reset Button

BACKGROUND OF THE INVENTION

As a fellow longtime football fan the applicant has been aware of the recent issues regarding player concussions. The applicant is not aware of any personal electronic devices which help train players to avoid such concussions.

The applicant applied his skill set to inventing such a device. The applicant believes the proposed device will prove an effective tool that will over time train players to adjust play to avoid concussions and add the desired element of safety to the game.

While its certainly plausible for the proposed device to serve professional football including in games the applicant envisions a more critical service in youth football.

I claim:

1. A personal football head impact annunciator module comprising: A self-contained electronic module having an integral loop strap for securing it to a football helmet's face mask, a DC power source embedded in the module, one or more shock sensors or accelerometers embedded in the module, a timer embedded in the module, one or more LED lamps oriented to be visible to the player and referees embedded in the module, wherein upon the player sustaining a blow to the helmet of an impact exceeding a preselected threshold level said shock sensor triggers said timer which couples said DC power source to the LED illuminating it for a preset time period.

2. The module in claim 1 wherein the DC power source is a battery permanently embedded in the module.

3. The module in claim 1 wherein the DC power source is a replaceable battery.

4. The module in claim 1 wherein the DC power source is a rechargeable battery.

5. The module in claim one wherein an audible annunciating electronic component is substituted for or included with the LED lamp.

6. The module in claim 1 wherein a test button is included for checking the integrity of the battery charge.

7. The module in claim 1 wherein a manual reset button which may require a special tool is included for clearing an annunciation.

8. A method of using the module as recited in claim 1 comprising:
- attaching the module to the helmet of a player;
- selecting a higher sensitively level if the sensor is used in youth football;
- monitoring via the sensor or accelerometer for an impact that exceeds the threshold level corresponding with the sensitivity level;
- triggering the timer if the impact exceeds the threshold; and
- illuminating an LED for a preset time.

9. A method of using the module as recited in claim 1 comprising:
- attaching the module to the helmet of a player;
- selecting a higher sensitively level if the sensor is used in practice than for a game;
- monitoring via the sensor or accelerometer for an impact that exceeds the threshold level corresponding with the sensitivity level;
- triggering the timer if the impact exceeds the threshold; and
- illuminating an LED for a preset time.

10. A method of using the module as recited in claim 1 comprising:
- attaching the module to the helmet of a player;
- monitoring via the sensor or accelerometer for an impact that exceeds the threshold level;
- triggering the timer if the impact exceeds the threshold;
- illuminating an LED for a preset time; and
- suspending the player who is wearing the helmet during the game.

11. A method of using the module as recited in claim 1 comprising:
- attaching the module to the helmet of a player;
- monitoring via the sensor or accelerometer for an impact that exceeds the threshold level;
- triggering the timer if the impact exceeds the threshold;
- illuminating an LED for a preset time; and
- having the player who is wearing the helmet exit the game.

12. The module in claim 1 wherein the attachment means is a loop strap, clip, or clamp which attaches the module directly to the facemask bars.

13. The module in claim 1 wherein the module is made of rubber.

14. The module in claim 1 wherein a number corresponding to the shock sensor g force sensitivity rating is embossed on said module.

15. The module in claim 1 wherein the shock sensor is replaceable.

16. The module in claim 1 wherein different timer periods indicate the level of impact.

* * * * *